(12) United States Patent
Kato et al.

(10) Patent No.: US 7,186,991 B2
(45) Date of Patent: Mar. 6, 2007

(54) MIXED IRRADIATION EVALUATION SUPPORT SYSTEM

(75) Inventors: Chiaki Kato, Kawasaki (JP); Jun'ichi Taguchi, Sagamihara (JP)

(73) Assignee: Hitachi, Ltd., Tokyo (JP)

( * ) Notice: Subject to any disclaimer, the term of this patent is extended or adjusted under 35 U.S.C. 154(b) by 1307 days.

(21) Appl. No.: 10/061,341

(22) Filed: Feb. 4, 2002

(65) Prior Publication Data

US 2003/0147495 A1 Aug. 7, 2003

(51) Int. Cl.
*A61N 5/10* (2006.01)
(52) U.S. Cl. .................... 250/492.1; 378/145
(58) Field of Classification Search ........... 250/492.1; 378/18, 62, 65, 97, 145
See application file for complete search history.

(56) References Cited

U.S. PATENT DOCUMENTS 3,980,885 A * 9/1976 Steward et al. ............. 250/307

FOREIGN PATENT DOCUMENTS

| JP | 10-223400 | 8/1998 |
|---|---|---|
| JP | 10-244013 | 9/1998 |
| JP | 10-511022 | 10/1998 |
| JP | 10-309324 | 11/1998 |
| JP | 11-019234 | 1/1999 |
| JP | 11-290466 | 10/1999 |
| JP | 2000-242722 | 9/2000 |

OTHER PUBLICATIONS

"Small volume Multiple non-coplanar Arc Radiotherapy (SMART) for tumors of the lung, head & neck and the abdominopelvic region," CAR'98 Proceedings, pp. 257-261.

* cited by examiner

*Primary Examiner*—Kiet T. Nguyen
(74) *Attorney, Agent, or Firm*—Mattingly, Stanger, Malur & Brundidge, P.C.

(57) ABSTRACT

A mixed irradiation evaluation support system for supporting judgment and determination of allocation of contribution in mixed irradiation using proton beams and X-rays. According to a composition ratio designated by a composition ratio scroll bar 107, a dose distribution by a proton beam and a dose distribution by an X-ray are composed, and the result of the composition is displayed three-dimensionally in a three-dimensional display part 104. Further, when a cross section is designated in the three-dimensional display part 104, an isodose map 115 in the designated cross section is displayed in a cross section window 114.

20 Claims, 8 Drawing Sheets

MIXED IRRADIATION EVALUATION SUPPORT SYSTEM

BACKGROUND OF THE INVENTION

The present invention relates to mixed irradiation using proton beams and X rays, and in particular, to a method of supporting treatment planning for effectively applying a certain dose of radiation on a focus (malignant tissue) while suppressing normal tissue's exposure to radiation.

In radiotherapy that uses radiation for treatment, it is desired that normal tissues' exposure to radiation is suppressed as much as possible while applying a sufficient therapeutic dose of radiation on a focus such as cancer. Accordingly, treatment planning is required before treatment, in order to judge and determine intensity and a direction of radiation to emit, utilizing image data obtained by a video diagnostic apparatus such as an X-ray CT (Computerized Tomography) unit, and based on results of simulation of a dose distribution or the like.

Generally, such treatment planning is carried out by software that runs on a computer system. First, in treatment planning, image data are used in order to set three-dimensional areas of a focus and noteworthy normal tissues around the focus, and their coordinates are stored into a memory. Next, a three-dimensional dose distribution inside a human body is calculated according to a certain physical model and using the image data, based on an irradiation range (called a radiation field), which is determined according to the size of the focus, and a tentatively-determined direction and intensity of irradiation.

Thus-obtained results are evaluated by various evaluation techniques. As such techniques, for example, may be mentioned DVH (Dose Volume Histogram), i.e., a graph expressing a relation between a dose and a tissue volume having a dose value thereof, an isodose map (isodose contour map) in which a dose distribution is superposed onto a body tomographic image, and three-dimensional displaying in which a dose distribution is superposed as three-dimensional data onto body tissues and is displayed semi-transparently and stereoscopically. When it is judged by these techniques that the dose distribution is desirable one, then, the tentatively-determined direction and intensity are employed for treatment. If not, the direction and intensity of irradiation are determined anew, and the dose distribution is calculated again to evaluate the results. Usually, in treatment planning, such operations are repeated to determine the direction and intensity of irradiation to be employed for treatment.

On the other hand, recently, proton treatment facilities have been constructed in various places of the world. In these facilities, a proton beam generated by an accelerator (particle accelerator) is used for treatment, and treatment by a proton beam is started in parallel with the conventional X-ray treatment. As an example of a proton treatment facility, may be mentioned Proton Treatment Center in Loma Linda University Medical Center in USA.

A proton beam used in proton beam treatment has a characteristic called "Bragg Peak". Namely, when a proton beam is irradiated onto a material, the dose increases rapidly to become the maximum at a certain depth from the surface, and decreases rapidly to zero in a deeper area than that depth. This location at which the dose becomes the maximum is called Bragg Peak. By controlling the location of Bragg Peak, it is possible to apply a large dose to a focus, generally conforming to the shape of the focus, and scarcely applying a dose to the back of the focus.

In contrast, an X-ray used in X-ray treatment has a characteristic that the dose declines exponentially according to the depth from a surface. Thus, the X-ray does not have Bragg Peak. Accordingly, in a usually-employed method, in order to suppress exposure of normal tissues as much as possible, radiation is applied from a plurality of directions toward a focus, in order to apply a large dose to the focus locally. For generating an X-ray, so large scale an accelerator is not required as in the case of a proton beam. Thus, conventionally, an X-ray has been widely used in medical facilities. X-ray treatment is described in Takuro Arimoto, et al.: "Small volume Multiple non-coplanar Arc Radiotherapy (Smart) for tumors of the lung, head&neck and abdominopelvic region", CAR' 98 Proceedings, pp. 257–261, for example.

SUMMARY OF THE INVENTION

Under such situations, doctors are beginning to have an interest in a treatment employing both a proton beam and an X-ray. A proton beam can apply a dose much more locally than an X-ray, that it can irradiate a focus with higher positioning accuracy. However, sometimes, it is difficult to judge how wide the focus extends, even by image data taken by a video diagnostic apparatus such as an X-ray CT unit. Accordingly, attention is attracted to a method in which an X-ray is more conveniently used to irradiate a focus widely, to reduce escaped areas. Further, it is possible to consider a method in which a focus is irradiated with an X-ray, and after the focus has shrunk, a proton beam is used to apply a dose locally. In those mixed irradiation methods, it is important to determine a value of a resultant dose from a dose of a proton beam and a dose of an X-ray, and a value of a composition ratio.

Conventionally, however, a dose of a proton beam and a dose of an X-ray are evaluated independently, and it is impossible to evaluate both in an integrated manner.

An object of the present invention is to provide a mixed irradiation evaluation support system that can evaluate a dose distribution of a proton beam and a dose distribution of an X-ray in an integrated manner.

A first mixed irradiation evaluation support system according to the present invention comprises: a means for composing dose distributions of proton beams and X-rays in a human body, according to a designated composition ratio; and a display means for displaying a composite dose distribution three-dimensionally. In this case, the display means may use different colors for a dose distribution of a proton beam and a dose distribution of an X-ray.

Further, a second mixed irradiation evaluation support system according to the present invention comprises: a means for composing dose distributions of proton beams and X-rays in a human body, according to a designated composition ratio; and a display means for displaying an isodose map in a designated cross section in the human body with respect to a composite dose distribution.

Further, a third mixed irradiation evaluation support system according to the present invention comprises: a means for composing dose distributions of proton beams and X-rays in a human body; and a display means for displaying a dose distribution on a designated line in the human body, with respect to a designated range of a composition ratio.

Further, a fourth mixed irradiation evaluation support system according to the present invention comprises: a means for composing dose distributions of proton beams and X-rays in a human body; and a display means for displaying a dose value at a designated point in the human body, with respect to a designated range of a composition ratio. In this case, the display means may display a dose distribution of a proton beam and a dose distribution of an X-ray superimposedly.

Further, a fifth mixed irradiation evaluation support system according to the present invention comprises: a means for composing dose distributions of proton beams and X-rays in a human body; and a display means for displaying DVH for a designated tissue in the human body, with respect to a designated range of a composition ratio.

Further, a sixth mixed irradiation evaluation support system according to the present invention comprises: a means for composing dose distributions of proton beams and X-rays in a human body; and a display apparatus for displaying a composite dose distribution three-dimensionally.

Further, a seventh mixed irradiation evaluation support system according to the present invention comprises: a means for composing dose distributions of proton beams and X-rays in a human body; and a display apparatus for displaying an isodose map in a designated cross section in the human body with respect to a composite dose distribution.

Further, an eighth mixed irradiation evaluation support system according to the present invention comprises: a means for composing dose distributions of proton beams and X-rays in a human body; and a display apparatus for displaying a dose distribution on a designated line in the human body, with respect to a designated range.

Further, a ninth mixed irradiation evaluation support system according to the present invention comprises: a means for composing dose distributions of proton beams and X-rays in a human body; and a display apparatus for displaying a dose value at a designated point in the human body, with respect to a designated range.

Further, a tenth mixed irradiation evaluation support system according to the present invention comprises: a means for composing dose distributions of proton beams and X-rays in a human body; and a display apparatus for displaying DVH for a designated tissue in the human body, with respect to a designated range.

Further, an eleventh mixed irradiation evaluation support system according to the present invention comprises: a means for composing dose distributions of proton beams and X-rays in a human body, according to a designated composition ratio; and a display apparatus for displaying a composite dose distribution three-dimensionally.

Further, a twelfth mixed irradiation evaluation support system according to the present invention comprises: a means for composing dose distributions of proton beams and X-rays in a human body, according to a designated composition ratio; and a display apparatus for displaying an isodose map in a designated cross section in the human body with respect to a composite dose distribution.

Further, a thirteenth mixed irradiation evaluation support system according to the present invention comprises: a means for composing dose distributions of proton beams and X-rays in a human body; and a display apparatus for displaying a dose distribution on a designated line in the human body, with respect to a designated range of a composition ratio.

Further, a fourteenth mixed irradiation evaluation support system according to the present invention comprises; a means for composing dose distributions of proton beams and X-rays in a human body; and a display apparatus for displaying a dose value at a designated point in the human body, with respect to a designated range of a composition ratio.

And, a fifteenth mixed irradiation evaluation support system according to the present invention comprises: a means for composing dose distributions of proton beams and X-rays in a human body; and a display apparatus for displaying DVH for a designated tissue in the human body, with respect to a designated range of a composition ratio.

In the above-described systems, when there are a plurality of irradiation directions with respect to at least one of proton beam and X-ray, then, respective dose distributions for irradiation directions of proton beams or X-rays may be composed with arbitrary intensity weights.

Further, each of the above-described systems may further comprise a means for inputting image data of the human body, and a means for calculating a dose distribution of a proton beam and a dose distribution of an X-ray in the human body, using the inputted image data.

DETAILED DESCRIPTION OF THE PREFERRED EMBODIMENTS

Now, referring to the drawings, embodiments of the present invention will be described.

First, outlines of methods of irradiating a proton beam and an X-ray will be described.

In the case of irradiating a proton beam, by arranging scatterers inside an irradiation apparatus in order to extend Bragg Peak, it is possible to control the characteristic, such that Bragg Peak becomes a flat area of a constant width. This flat area is called SOBP (Spread Out of Bragg Peak). Further, the location of SOBP can be controlled by adjusting the incident energy of the proton beam of the irradiation apparatus. Accordingly, when the water equivalent depth from a body surface to a focus and the water equivalent thickness of the focus in the depth-wise direction are known, it is possible to make SOBP coincide with the focus satisfactorily. The water equivalent depth from the body surface to the focus and the water equivalent thickness of the focus in the depth-wise direction are obtained from image data taken by an X-ray CT unit.

Figure 7:
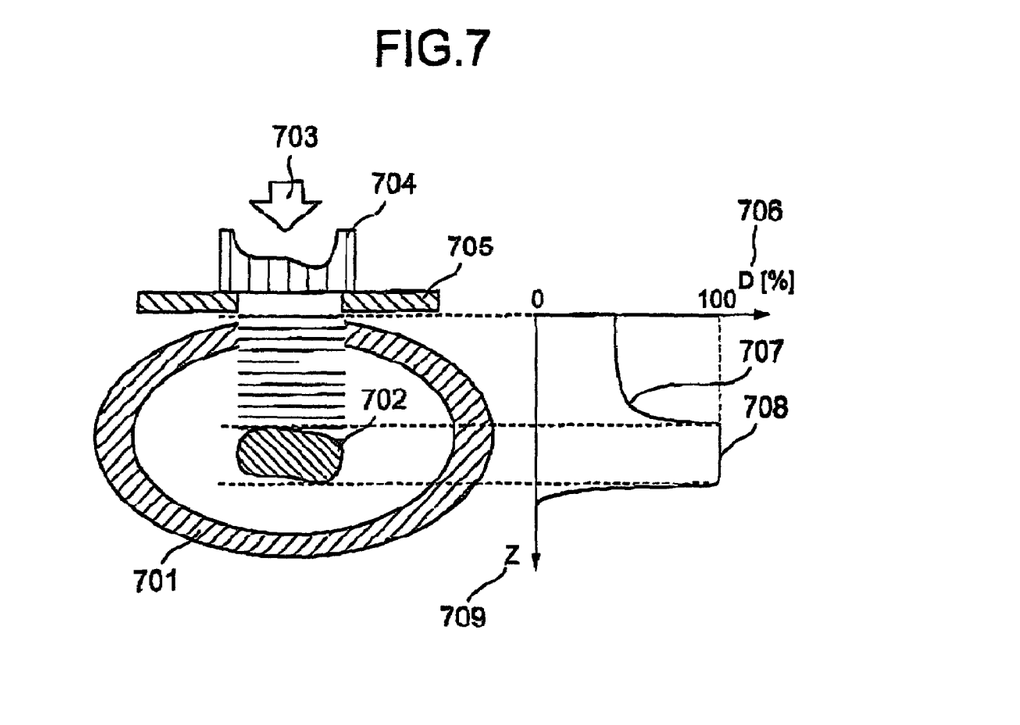
FIG. 7 is a view showing a state of proton beam radiation.

FIG. 7 is a view showing a state of proton beam irradiation. As shown in the figure, a proton beam 703 is irradiated to a focus 702 inside a human body 701 through a bolus 704 and a patient collimator 705. A graph shown in the right side of the figure is a graph showing a depth dose distribution 707 by irradiation of the proton beam 703. In this graph, the horizontal axis D 706 shows a relative dose [%] when the dose at SOBP 708 is taken as 100%, and the vertical axis z 709 shows the depth in the direction of irradiation of the proton beam.

The bolus 704 is a kind of a distance compensating filter, and has a role of making the back end of SOBP 708 coincide with the back end of the focus 702. The shape of the bolus 704 is determined such that the water equivalent depth from the bolus 704 to the back end of the focus 702 has a constant value. In that case, the depth dose distribution 707 at the time of irradiation of the proton beam 703 is determined such that SOBP 708 coincides with the focus 702. The patient collimator 705 limits the irradiation range such that the proton beam is not irradiated outside the focus 702 in the lateral direction.

On the other hand, in the case of X-ray irradiation, a bolus is not required, and an X-ray is simply irradiated toward a focus.

Next, will be described a treatment system by a proton beam or an X-ray, to which the present invention can be applied. The case of proton beam is taken as an example, since both cases are substantially equivalent as a treatment system.

Figure 8:
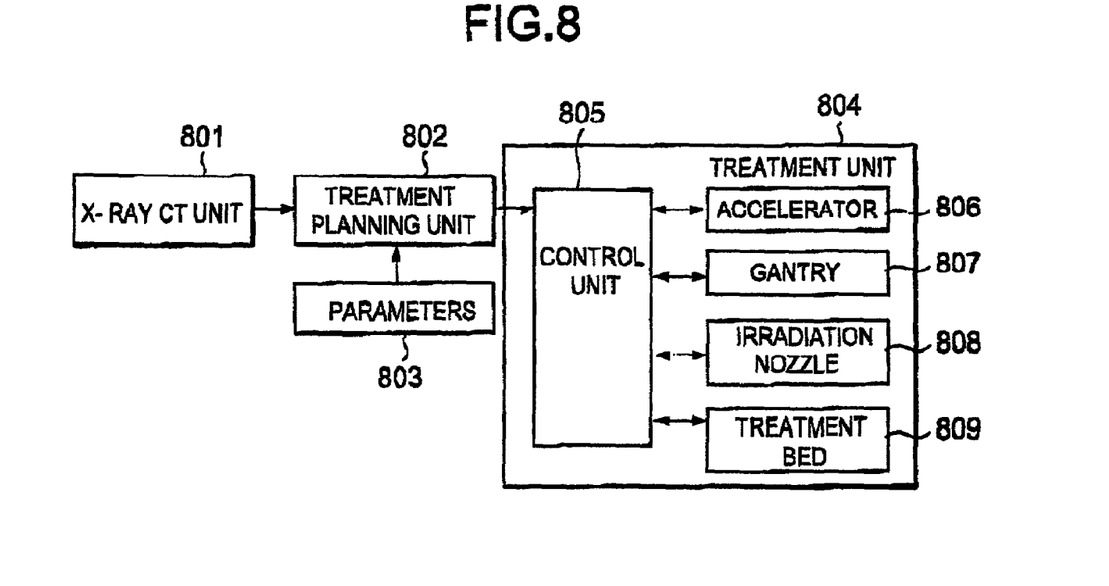
FIG. 8 is a diagram showing an example of a treatment system.

FIG. 8 is a diagram showing an example of a treatment system by a proton beam, to which the present invention can be applied.

As shown in the figure, the treatment system comprises an X-ray CT unit 801, a treatment planning unit 802, and a treatment unit 804. Further, the treatment unit 804 comprises an accelerator 806, a gantry 807, an irradiation nozzle 808, a treatment bed 809, and a control unit 805 for controlling them.

The X-ray CT unit 801 obtains body tomographic images of a human body as an object of treatment. The body tomographic images obtained by the X-ray CT unit 801 are inputted into the treatment planning unit 802. The treatment planning unit 802 calculates a dose distribution based on various parameters 803, and evaluates and judges the results of the calculation. These parameters 803 are changed several times to determine the optimum irradiation conditions. The irradiation conditions determined are inputted to the control unit 805 in the treatment unit 804.

According to the received irradiation conditions, the control unit 805 controls the maximum range of the proton beam, SOBP of the proton beam, an angle of rotation of the gantry 807, parameters of various devices arranged in the irradiation nozzle 808, and a position and angle of rotation of the treatment bed 809.

Figure 9:
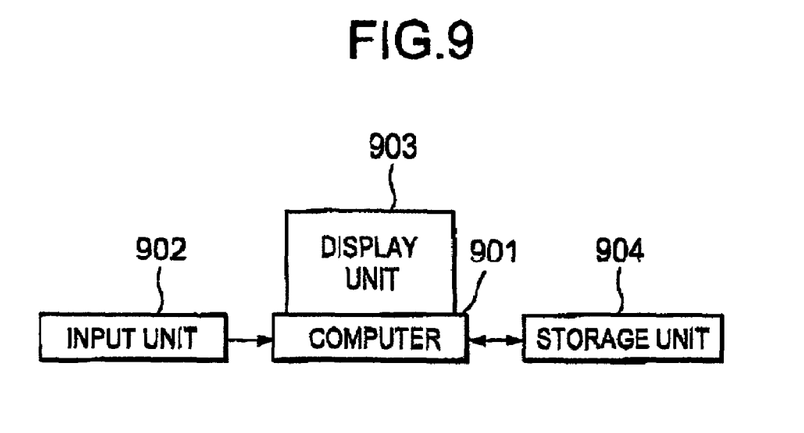
FIG. 9 is a diagram showing a computer system for implementing a treatment planning unit.

FIG. 9 is a diagram showing a computer system for implementing the treatment planning unit 802. As shown in the figure, this system comprises a main body of a computer 901, an input unit 902 for inputting data such as image data and an operator's instruction, a display unit 903 for displaying results, and a storage unit 904 for saving treatment planning software itself and output results.

A mixed irradiation evaluation support system according to the present invention is implemented, for example, as software that operates in the treatment planning unit 802, and can be distributed through a portable storage medium such as a floppy disk or CD-ROM or a means such as a network.

Figure 10:
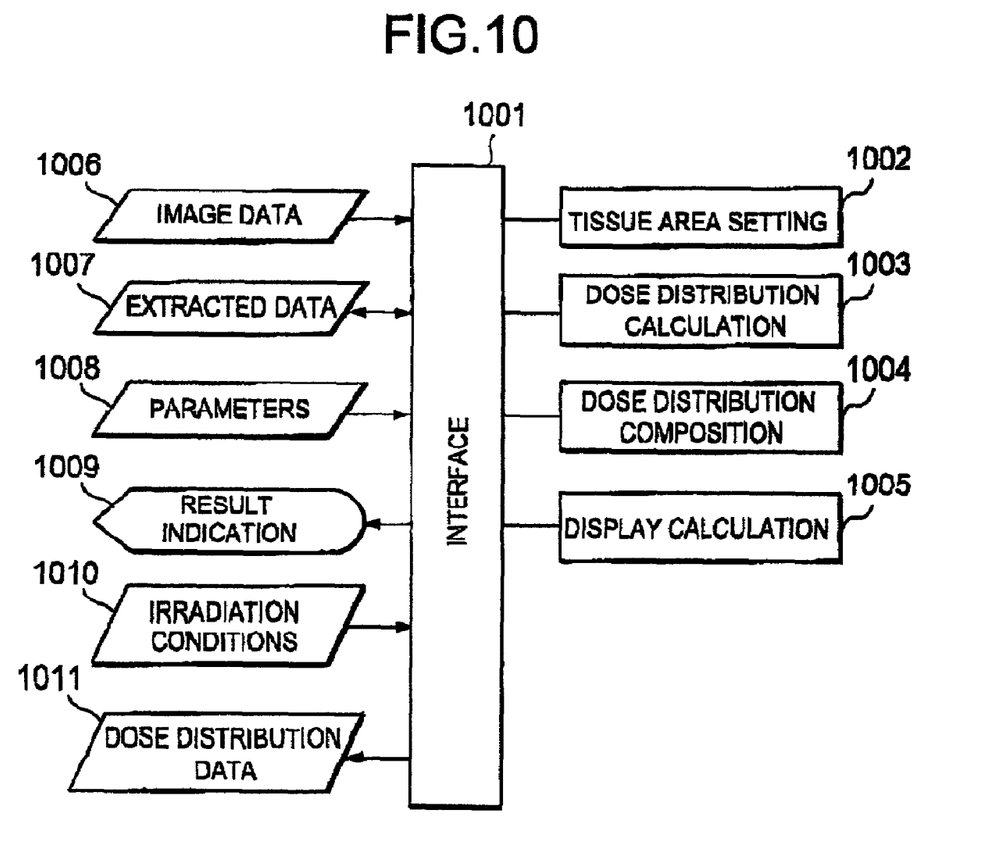
FIG. 10 is a diagram showing a functional configuration of a treatment planning unit.

FIG. 10 is a diagram showing a functional configuration of the treatment planning unit 802, As shown in the figure, the treatment planning unit 802 comprises processing means such as a tissue area setting means 1002, a dose distribution calculation means 1003, a dose distribution composition means 1004, and a display calculation means 1005. Each processing means outputs and/or inputs image data 1006, extracted data 1007, parameters 1008, result indication 1009, irradiation conditions 1010, dose distribution data 1011, and the like into and/or from the storage unit 904 and the display unit 903 through an interface 1001 as an input-output unit.

Next, details of each processing means will be described. In the following processing, image data 1006 taken by the X-ray CT unit or the like are used. Here, the image data mean a three-dimensional array consisting of voxels for storing image densities.

The tissue area setting means 1002 is provided for obtaining three-dimensional coordinates of body tissues as a whole, a focus, and important tissues, from three-dimensional data stored in a three-dimensional array consisting of voxels. The tissue area setting means 1002 sets a tissue area, for example, by a semi-automatic extract method such as a method using a threshold for an image density or an area extension method using connection information of a tissue, or by an area designation method in which a man traces a noted tissue area in each slice image outputted onto the display unit The dose distribution calculation means 1003 calculates a dose distribution by a dose distribution calculation method based on a physical model of a proton beam and by a dose distribution calculation method based on a physical model of an X-ray. For example, a dose distribution of a proton beam is calculated by a broad beam method, and a dose distribution of an X-ray is calculated by TPR (Tissue Peak Ratio) method. The dose distribution calculation means 1003 performs calculation of a dose distribution under the condition that the shape of the collimator is determined, and outputs the dose distribution as voxel data stored in a three dimensional array. When there are a plurality of directions of proton beam or X-ray radiation, calculation of a dose distribution is performed for each of the plurality of irradiation directions, and the dose distribution for each irradiation direction is outputted.

The dose distribution composition means 1004 composites a dose distribution of a proton beam and a dose distribution of an X-ray, by adding those dose distributions as voxel data, at a designated composition ratio. The value of the composite dose may be normalized by a dose value at an arbitrary point. Further, when there are a plurality of directions with respect to proton radiation or X-ray radiation, dose distributions for respective irradiation directions are added as voxel data, with arbitrary intensity weighting.

The display calculation means 1005 performs three-dimensional displaying, isodose map displaying, DVH displaying, and the like.

In the case of the three-dimensional displaying, the display calculation means 1005 superposes three-dimensionally body tissues as three-dimensional distribution data and a dose distribution, to display both the body tissues and dose distribution semi-transparently onto a two-dimensional projection surface. Further, the display calculation means 1005 changes three-dimensional displaying correspondingly to a change in the designated composition ratio. By three-dimensional displaying, it is possible to grasp intuitively the positional relation between a tissue and a dose distribution in the three-dimensional space.

Further, in the case of isodose map displaying, the display calculation means 1005 displays isodose lines superposed on a designated body cross section. An isodose map consists of lines each connecting points of an equal dose value, similarly to a contour map. An isodose map contributes to quantitative understanding of a positional relation between a tissue and a dose distribution.

In the case of DVH displaying, the display calculation means 1005 displays a graph relating to an object tissue whose area has been set, i.e., a target tissue, a normal tissue, or photographed body tissues as a whole. The horizontal axis of the graph indicates a dose and a vertical axis indicates a volume, and the graph shows, for each dose volume, the total volume of a tissue or tissues at which a dose value is larger than the dose valley in question. In that case, scales of the horizontal and vertical axes may be changed independent of each other. By employing DVH, it is possible to know how much volume in the target tissue is irradiated more than the lethal dose, and how much volume in the normal tissue is irradiated less than the tolerant dose. By seeing DVH for the body tissues as a whole, it is possible to know to what degree a dose is dispersed on the whole. And, it can be said that treatment planning in which as much volume as possible lies in a lower dose area is favorable planning. In the case of DVH, it is possible to quantitatively evaluate a dose distribution as it result of calculation.

Further, the display calculation means 1005 also performs display in another way than the above-mentioned. Its details will be described later.

Next, general operation of the treatment planning unit 802 will be described.

When treatment planning is performed using the treatment planning unit 802, image data 1006 are inputted first. Then, an extraction range and the like are designated by the parameters 1008, to obtain an extraction result by the tissue area setting means 1002. The result is saved as extraction data 1007 into the storage unit 904. In this case, for example, one focus and a plurality of important tissues are set.

Next, with respect to each X-ray or proton beam, irradiation conditions 1010 are inputted. And, each time, operation by the dose distribution calculation means 1003 is repeated. Its result is evaluated in order to obtain final irradiation conditions 1010 and dose distribution data 1011, and these are saved into the storage unit 904. In the course of this processing, the display calculation means 1005 outputs, for example, a state of the dose distribution in question as the result indication 1009.

Next, mixed irradiation of an X-ray and a proton beam is evaluated. To this end, first, the dose distribution composition means 1004 performs processing that uses the image data 1006, the extraction data 1007, and the dose distribution data 1011, while specifying the parameters 1008 including a mixing ratio and the like.

Then, the display calculation means 1005 displays the results as the result indication 1008 in the form of three-dimensional display, an isodose map, a relation between a dose and DVH, or a relation between a dose and a composition ratio. Each time the parameters 1008 such as the mixing ratio and the like are designated, the result indication 1008 is given. Thus, the final mixing ratio is obtained and saved into the storage unit 904.

Next detailed operation of the treatment planning unit 802 will be described.

Figure 1:
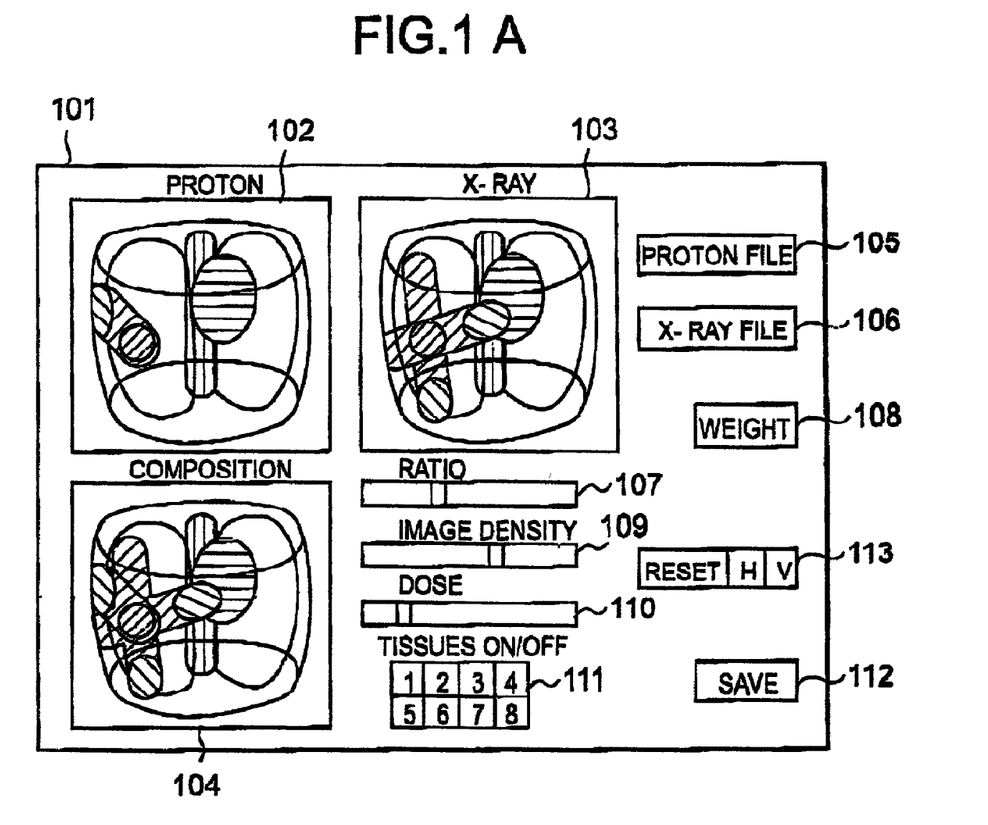
FIGS. 1A and 1B are views showing an example of a screen layout.

FIG. 1 is a view showing an example of a layout of a screen displayed on the display unit 903 of the treatment planning unit 802 according to the present invention.

As shown in FIG. 1A, a three-dimensional display window 101 includes three-dimensional display parts 102–104, a proton file pull-down menu 105, an X-ray file pull-down menu 106, a composition ratio scroll bar 107, a weight setting button 108, an image density scroll bar 109, a dose scroll bar 110, a tissue display/non-display selection column 111, a save button 112, and a section designation button 113.

The three-dimensional display part 102 is an area for displaying a proton beam dose distribution three-dimensionally, the three-dimensional display part 103 for displaying an X-ray dose distribution three-dimensionally, and the three-dimensional display part 104 for displaying a composite dose distribution of both proton beam and X-ray.

When a mouse cursor is dragged in one of the three-dimensional display parts 102, 103 and 104, an object of the three-dimensional display is rotated according to the drag distance in all the three-dimensional display parts 102, 103 and 104.

The proton file pull-down menu 105 is used for reading proton beam dose distribution data that have been calculated in advance. When the proton file pull-down menu 105 is clicked by the mouse, a menu for selecting a proton file is displayed, for example. When a desired file is selected, dose distribution data for a proton beam are read into a memory or the like.

The X-ray file pull-down menu 106 is used for reading X-ray dose distribution data that have been calculated in advance. When the X-ray file pull-down menu 106 is clicked by the mouse, a menu for selecting an X-ray file is displayed. When a desired file is selected, dose distribution data for an X-ray are read into the memory or the like.

The weight setting button 108 is a button for setting a weight for each irradiation direction when there are a plurality of irradiation directions. When the weight setting button 108 is clicked, another window is opened, and a weight for each irradiation direction can be set in the opened window.

The composition ratio scroll bar 107 is used for setting a value of the composition ratio between a proton beam and an X-ray. By dragging the composition ratio scroll bar 107 using the mouse cursor, an operator changes and designates the value of the composition ratio. After the designation of the composition ratio, display of the three-dimensional display part 104 for the composition dose distribution is updated according to the designated composition ratio.

The image density scroll bar 109 is used for setting an image density value (a threshold) of images displayed in the three-dimensional display parts 102–104. Tissues etc. having density values larger than the value designated by the image density scroll bar 109 are displayed in the three-dimensional display parts 102–104. By dragging the image density scroll bar 108 using the mouse cursor, the operator changes and designates the image density value. After the designation of the image density, the three-dimensional displays are updated in all the three-dimensional display parts 102, 103 and 104 according to the designated image density.

The dose scroll bar 110 is used for setting a dose value (a threshold) displayed in the three-dimensional display parts 102–104. Dose distributions having dose values larger that the value designated by the dose scroll bar 110 are displayed in the three-dimensional display parts 102–104. By dragging the dose scroll bar 110 using the mouse cursor, the operator changes and designates the dose value. After the designation of the dose value, the three-dimensional displays are updated in all the three-dimensional display parts 102, 103 and 104 according to the designated dose value.

The tissue display/non-display selection column 111 is used for controlling display/non-display of tissues designated in the tissue area setting. The tissues designated in the tissue area setting are numbered and registered. When a certain number in the tissue display/non-display selection column 111 is picked by the mouse cursor, its background color is changed if there is a tissue corresponding to the number. And, the tissue becomes hidden in all the three-dimensional display parts 102, 103 and 104. When the number is picked again, its background color returns to the former color, and the tissue in question returns to the displayed state.

The section designation button 113 is used for determining if a horizontal cross section is to be obtained (a horizontal section mode) or a vertical cross section is to be obtained (a vertical section mode) when the mouse cursor is picked in the three-dimensional display parts. When the "H" part of the section designation button 113 is picked by the mouse cursor, the horizontal mode is selected. And, when the "V" part of the section designation button 113 is picked by the mouse cursor, the vertical mode is selected. When one of those parts is picked, the background color of the picked part changes, showing which mode is selected. Here, when the "Reset" part of the section designation button 113 is picked, the background color of the "H" or "V" part returns to the former color, and the vertical section mode or the horizontal section mode returns to a state where no section mode is selected.

In a state where one of the section modes is selected, when the mouse cursor is picked, for example, in the three-dimensional display part 104 for displaying a composite dose distribution, then, a horizontal or vertical line is displayed at that position, depending on the designated section mode. Then, a section window 114 as shown in FIG. 1B is opened to display an isodose map 115 on the basis of a body tomographic image at that position.

The save button 112 is used for saving the final weight and composition ratio into the storage unit 904. When the save button 112 is clicked, for example, a window for designating a save file is opened, and the data are saved into the designated file.

Next, processing in the present embodiment will be described based on a detailed operation example.

First, will be described the case where effect of the composition ratio on the composite dose is evaluated by three-dimensional displaying. This is suitable for stereoscopically grasping if a sufficient dose is applied to a focus, or if a large dose is not applied to normal tissues around the focus, for example by rotational displaying.

In this case, three-dimensional displaying is employed, and thus, a dose distribution is displayed by isodose surfaces each corresponding to a dose value designated. Further, in the case of the composite dose distribution, different colors are used to display three-dimensionally a proton beam dose distribution and an X-ray dose distribution. By this, it is possible to ascertain, at a glance, degree of contribution by each dose distribution.

In the case of three-dimensional displaying, by changing the image density value, it is possible to display only the body surface, to display the inner parts transparently, or to display only the bones. Or, when a dose distribution is not seen in the shadow of a certain tissue, it is possible to make the tissue hidden.

Figure 2:
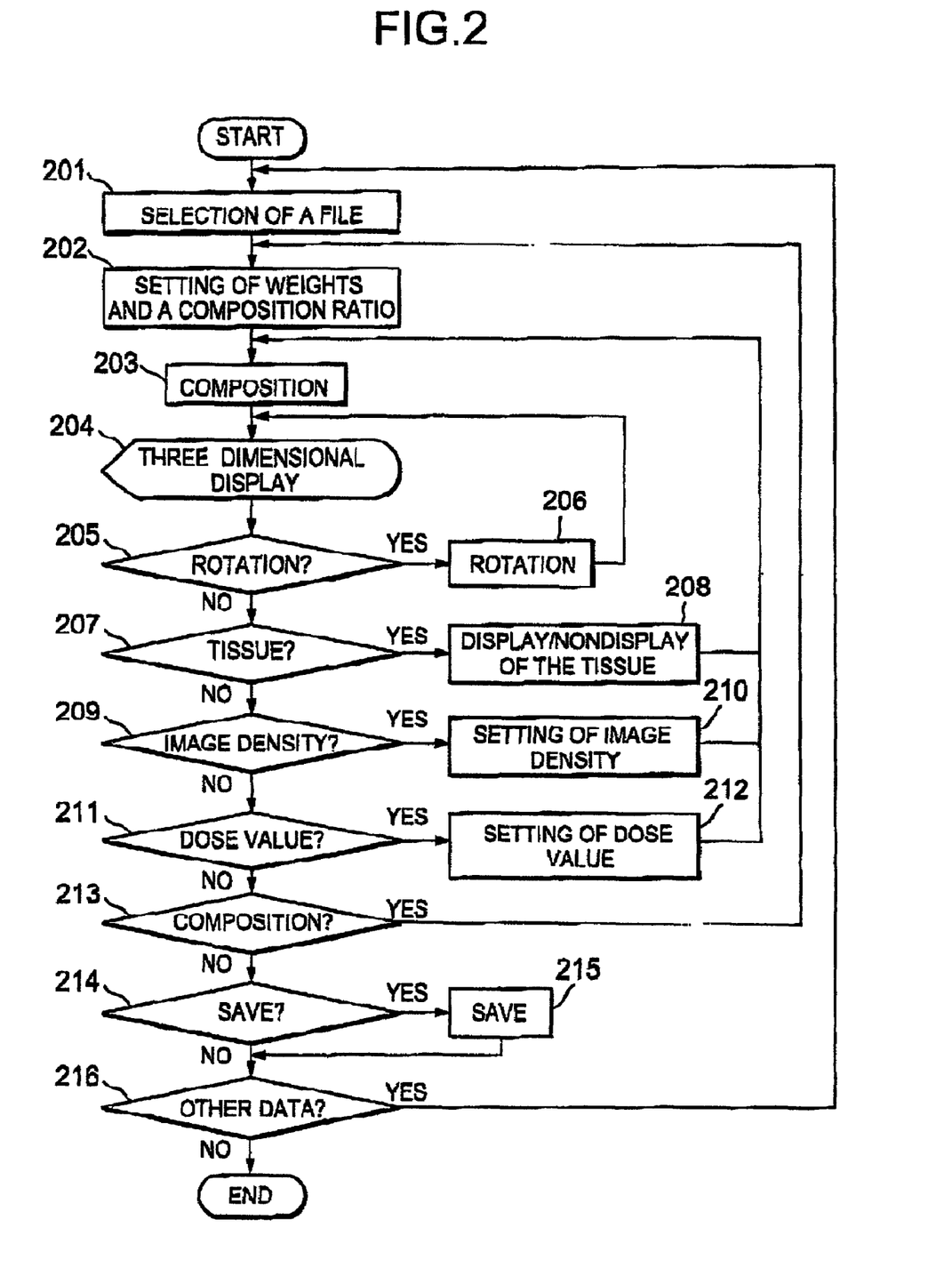
FIG. 2 is a flowchart showing a flow of processing in the case of three-dimensional displaying.

FIG. 2 is a flowchart for showing a flow of detailed processing in the case of three-dimensional displaying.

[Step 201] Selection of a File

First, when a file of proton beam dose distribution data and a file of X-ray dose distribution data are selected, each dose distribution data stored in a three-dimensional array are read.

[Step 202] Setting of Weight and a Composition Ratio

Next, a weight for each irradiation direction and a value of the composition ratio are set. In this case, respective weights of irradiation directions and the value of the composition ratio may be set to their default values. Or, values designated by the operator may be set.

[Step 203] Composition

Dose distribution data of proton beam and X-ray stored in three dimensional arrays are added using the set weight for each irradiation direction and the set composition ratio.

[Step 204] Three-Dimensional Displaying

The dose distribution of proton beam, the dose distribution of X-ray, and the composite dose distribution are displayed three-dimensionally in the three-dimensional display parts in the three-dimensional display window, using default image density value, dose value, and angle of rotation (viewpoint).

In this case, different colors are used for displaying the proton beam dose distribution and X-ray dose distribution, and the composite dose distribution of them is displayed three-dimensionally using those different colors such that their contributes are seen. Further, all the tissues designated in the tissue area setting are displayed in the default state.

[Step 205] Judgment of Rotation

When the mouse cursor is dragged in a three-dimensional display part, the flow proceeds to Step 206. Otherwise, the flow proceeds to Stop 207.

[Step 206] Rotation

The viewpoint is moved to the direction of the drag by the mouse cursor. And, an image projected on a plane that is vertical to that direction is calculated. To display the calculated image three-dimensionally, the flow returns to Step 204.

[Step 207] Judgment of Display/Non-display of Tissues

When the tissue display/non-display selection column 111 is picked, and if the tissue corresponding to the picked number is registered, then, the flow proceeds to Step 208. Otherwise, the flow proceeds to Step 209.

[Step 208] Display/Non-Display of Tissues

The number picked in the display/non-display selection column 111 is changed in its background color. Then, when the picked tissue is displayed in all the three-dimensional display parts, its state is changed to non-display. On the other hand, when the picked tissue is not displayed, its state is changed to display.

[Step 209] Judgment of Image Density Setting

When the image density scroll bar is dragged by the mouse cursor, the flow proceeds to Step 210. Otherwise, the flow proceeds to Step 211.

[Step 210] Setting of Image Density

The display state is changed such that tissues having density values larger than the value designated by the image density scroll bar are displayed.

[Step 211] Judgment of Dose Value Setting

When the dose scroll bar is dragged by the mouse cursor, the flow proceeds to Step 212. Otherwise, the flow proceeds to Step 213.

[Step 212] Setting of Dose Values

The display state is changed such that dose distributions having dose values larger than the value designated by the dose value scroll bar are displayed.

[Step 213] Judgment of Composite Ratio Setting

When the weight setting button for setting respective weights of irradiation directions is clicked, or when the composition ratio scroll bar is dragged by the mouse cursor, then, the flow returns to Step 202. Otherwise, the flow proceeds to Step 214.

[Step 214] Judgment of Save

When save of the weights and composition ratio is instructed, the flow proceeds to Step 215. Otherwise, the flow proceeds to Step 216.

[Step 215] Save

The weights and composition ratio are saved into storage unit, being attached with a file name.

[Step 216] Judgment of Input of Another File

When other data are to be read, the flow returns to Step 201. Otherwise, the processing is ended.

As described above, by three-dimensional displaying, the best weights and composition ratio can be determined.

Next, will be described the case where effect of the composition ratio on the composite dose is evaluated by using an isodose map. In this case, it is possible to grasp if a sufficient dose is applied to a focus or if a large dose is not applied to normal tissues around the focus, from the contours of a dose distribution displayed on a tomographic image of a body tissue. Further, this method is suitable for evaluating two-dimensionally and quantitatively how distant a certain isodose line is from a noted tissue.

In this case, a noted cross section is designated in three-dimensional display. When the section mode is designated by the section designation button 113, and thereafter, the mouse cursor is picked in the three-dimensional display part 104 for the composition dose distribution, then, a horizontal or vertical line is displayed at that position according to the section mode. Thereafter, the section window 114 as shown in FIG. 1B is opened to display an isodose map 115 on the basis of a body tomographic image at that position. In the isodose map 115, it is possible to specify the number of isodose lines or the dose values of isodose lines to be displayed.

Figure 3:
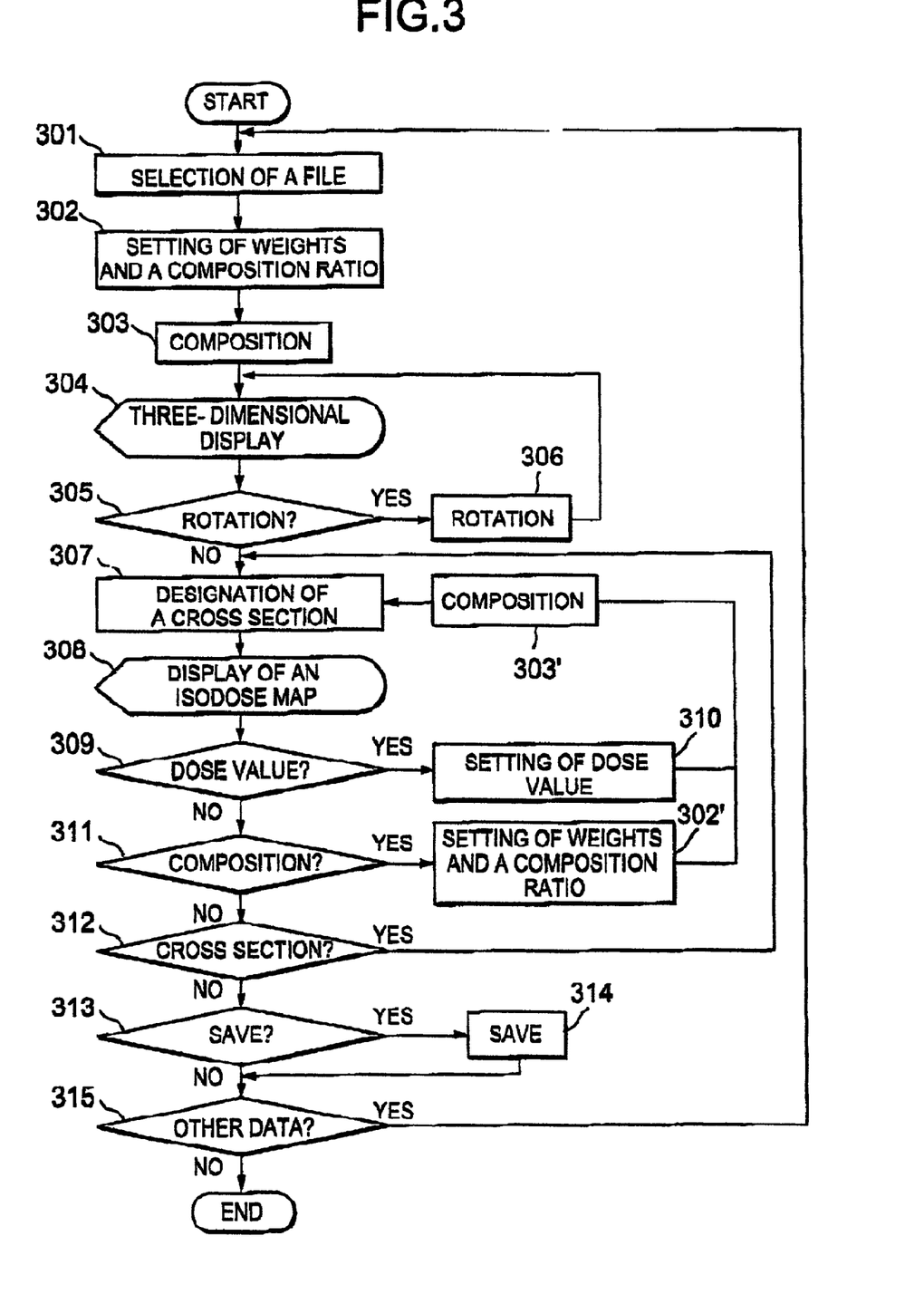
FIG. 3 is a flowchart showing a flow of processing in the case of isodose map displaying.

FIG. 3 is a flowchart showing a flow of detailed processing in this case.

Processing in Steps 301–306 is similar to the above-described processing in Steps 201–206 of FIG. 2, and its description is omitted.

[Step 307] Designation of a Cross Section

After the horizontal section mode or vertical section mode is selected, a cross section is designated by picking the mouse cursor in the three-dimensional display part for the composite dose distribution.

[Step 308] Display of an Isodose Map

An isodose map for the designated cross section is displayed. In this case, isodose lines are displayed by default isodose values.

[Step 309] Judgment of Isodose Value Setting

When an instruction is given to set dose values of isodose lines displayed in an isodose map, the flow proceeds to Step 310. Otherwise, the flow proceeds to Step 311.

[Step 310] Setting of Dose Values

Dose values of the isodose lines to be displayed in an isodose map are set.

[Step 311] Judgment of Composition Ratio Setting

When the weight setting button for setting respective weights of irradiation directions is clicked, or when the composition ratio scroll bar is dragged, then, the flow proceeds to Step 302'. Otherwise, the flow proceeds to Step 312.

[Step 302'] Setting of the Weights and Composition Ratio

Respective weights for irradiation directions and the composition ratio are set to the designated values.

[Step 303'] Composition

Using the respective weights for irradiation directions and composition ratio, which have been newly set, dose distribution data of proton beams and X-rays are added.

[Step 312] Judgment of Cross Section Designation

When an instruction is given to designate a cross section anew, the flow returns to Step 307. Otherwise, the flow proceeds to Step 313.

Thereafter, processing in Steps 313–315 follows. The processing in Steps 313–315 is similar to the processing in Steps 214–215 of FIG. 2, and its description is omitted.

As described above, by using an isodose map, it is possible to determine the best weights and composition ratio.

Next, will be described the case where, when a line (a line 116 in FIG. 1B) is also designated on a designated cross section, a dose distribution (dose profile) on the line is stereoscopically displayed as a function of the composition ratio, and effect of the composition ratio on the composite dose is evaluated based on this display.

In this case, all over the range (0–100%) of the composition ratio, a dose distribution on the designated line is calculated for each composition ratio at a prescribed resolution (for example, at intervals of 1%), and dose values are displayed stereoscopically in a coordinate system having an axis of a position on the line and an axis of a composition ratio. By such operation, data are displayed all over the range (0–100%) of the composition ratio, and thus, positions sensitive to the composition ratio, hardly-sensitive positions, etc. on the designated line can be seen at a glance.

Here, data does not need to be displayed not all over the range (0–100%) of the composition ratio. For example, when a rough composition ratio is determined by three-dimensional display or an isodose map, data may be displayed only for a partial range around the composition ratio in question.

Next, detailed processing in this case will be described.

Figure 4:
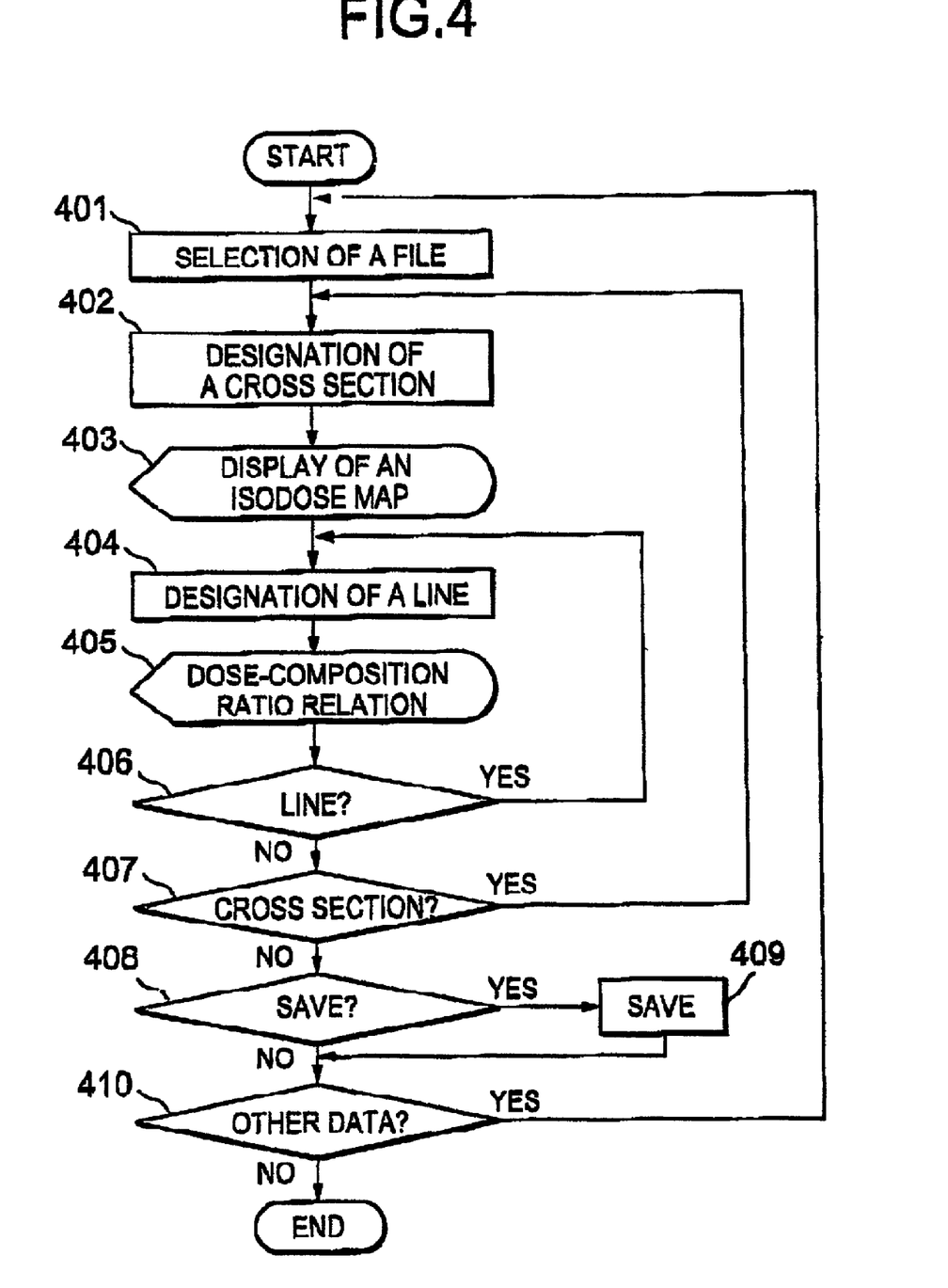
FIG. 4 is a flowchart showing a flow of processing in the case where a dose distribution is displayed stereoscopically as a function of a position in a straight line and a composition ratio.

FIG. 4 is a flowchart for showing a flow of detailed processing in this case.

Processing from selection of a file until display of an isodose map (Steps 401, 402 and 403) is similar to the above-described processing in Steps 301, 307 and 303 of FIG. 3, and its description is omitted.

[Step 404] Designation of a Line

When the mouse cursor is dragged on an isodose map, a line is designated.

[Step 405] Display of a Relation Between a Dose and a Composition Ratio

Dose values are displayed in a coordinate system having an axis of a position on the line and an axis of a composition ratio.

[Step 406] Judgment of Line Designation

When a line is to be designated anew, the flow returns to Step 404. Otherwise, the flow proceeds to Step 407.

[Step 407] Judgment of Cross Section Designation

When a cross section is to be designated anew, the flow returns to Step 402. Otherwise, the flow proceeds to Step 408.

Thereafter, processing in Steps 408–410 follows. The processing in Steps 408–410 is similar to the above-described processing in Steps 214–215 of FIG. 2, and its description is omitted.

Next, will be described the case where, when a point (a point 117 in FIG. 1B) is designated on the line on the designated cross section, a dose value at that point is displayed in a graph as a function of the composition ratio, and effect of the composition ratio on the composite dose is evaluated based on this display.

In this case, all over the range (0–100%) of the composition ratio, or in a partial range, a dose value at the designated point is calculated for each composition ratio at a prescribed resolution. The results of the calculation are displayed in a graph. By such operation, the above-mentioned effect can be evaluated with respect to each point, and thus, detailed investigation can be made.

Further, in this case, when a proton beam dose distribution and an X-ray dose distribution are displayed superimposedly in a graph, each contribution can be ascertained at a glance.

Next, detailed processing in this case will be described.

Figure 5:
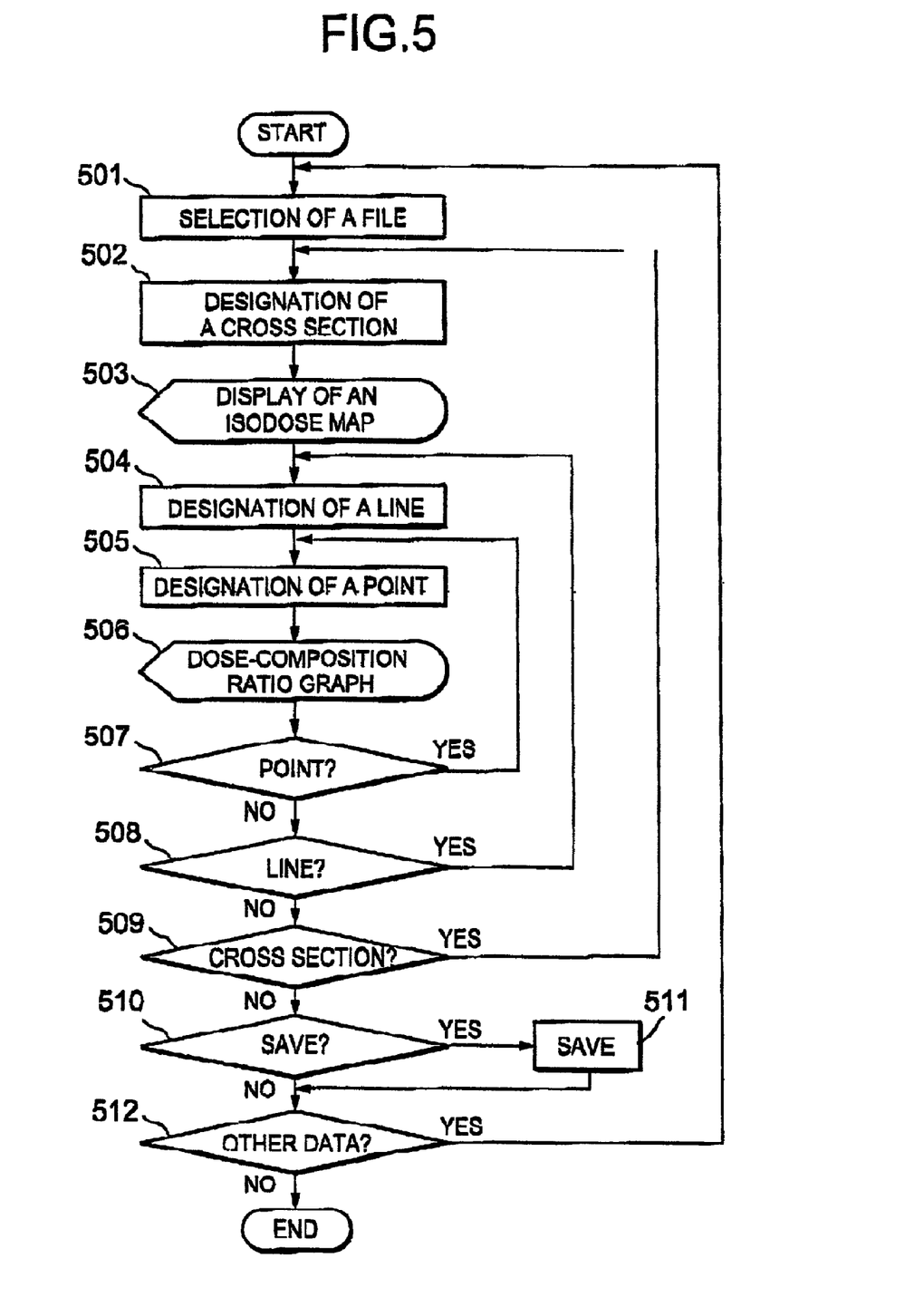
FIG. 5 is a flowchart showing a flow of processing in the case where a dose value at a designated point is displayed as a function of a composition ratio.

FIG. 5 is a flowchart for showing a flow of detailed processing in this case.

Processing from selection of a file until designation of a line (Steps 501–504) is similar to the above-described processing in Steps 401–404 of FIG. 4, and its description is omitted.

[Step 505] Designation of a Point

By picking the mouse cursor on a designated line, a point is designated.

[Step 506] Display of a Dose-Composition Ratio Graph

A graph showing a relation between a dose and a composition ratio on the designated point is displayed. At this time, a proton beam dose distribution and an X-ray dose distribution are also displayed superimposedly.

[Step 507] Judgment of Point Designation

When a point is to be designated anew, the flow returns to Step 505. Otherwise, the flow proceeds to Step 508.

[Step 508] Judgment of Line Designation

When a line is to be designated anew, the flow returns to Step 504. Otherwise, the flow proceeds to Step 509.

[Step 509] Judgment of Cross Section Designation

When a cross section is to be designated anew, the flow returns to Step 502. Otherwise, the flow proceeds to Step 510.

Thereafter, processing in Steps 510–512 follows. The processing in Steps 510–512 is similar to the above-described processing in Steps 214–215 of FIG. 2, its description is omitted.

Next, will be described the case where DVH for a tissue whose area is designated or for body tissues as a whole is displayed stereoscopically as a function of the composition ratio, and effect of the composition ratio on the composite dose is evaluated.

In DVH, a horizontal axis shows a dose, and a vertical axis shows a tissue volume of a certain dose or larger. In this case, all over the range (0–100%) of the composition ratio, or only in a partial range, DVH is obtained for each composition ratio at a prescribed resolution. In this DVH, a tissue volume is displayed with respect to an axis of a dose and an axis of the composition ratio. This is suitable for evaluating the above-mentioned effect for each tissue.

Next, detailed processing in this case will be described.

Figure 6:
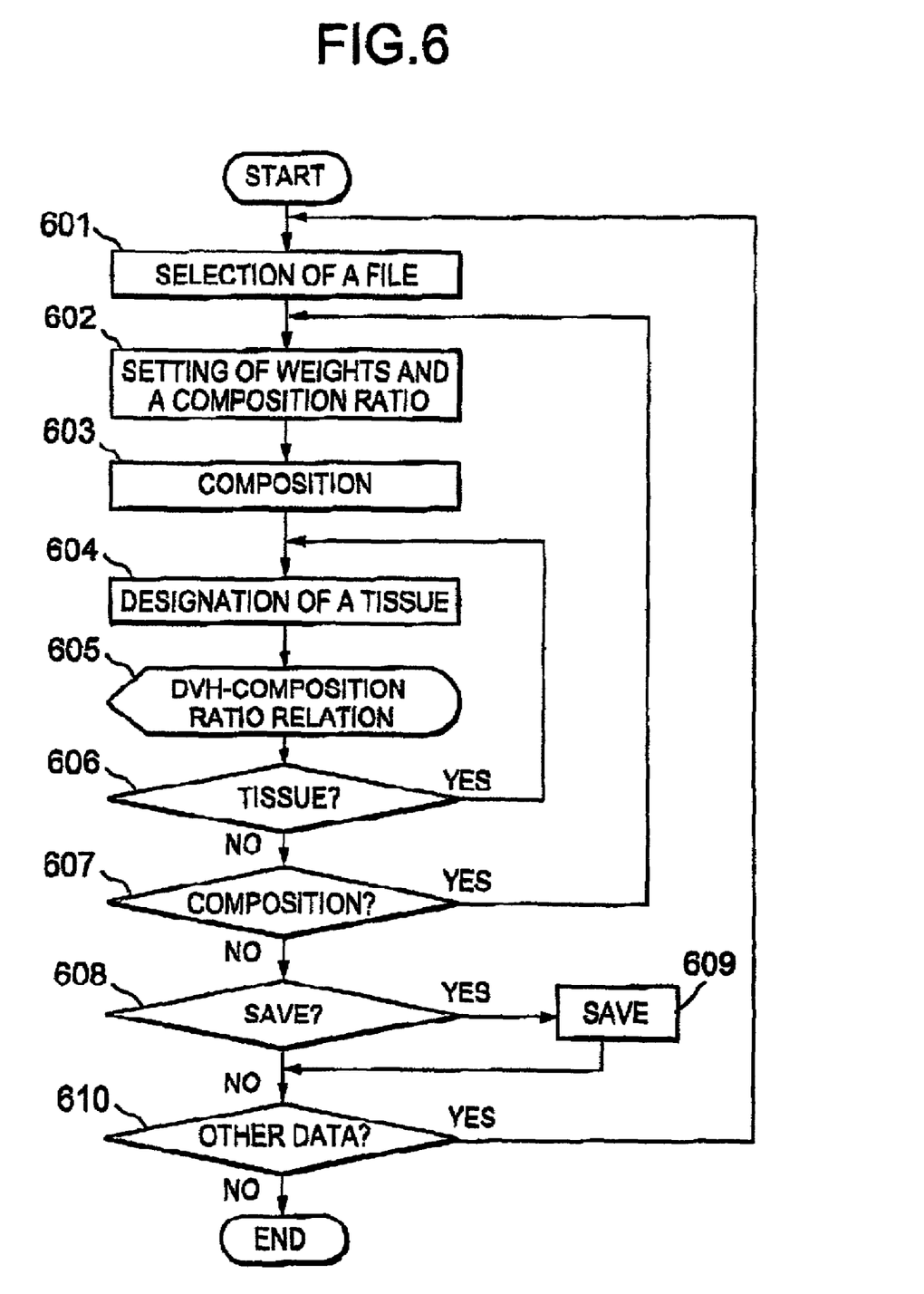
FIG. 6 is a flowchart showing a flow of processing in the case where DVH is displayed stereoscopically as a function of a composition ratio.

FIG. 6 is a flowchart for showing a flow of detailed processing in this case.

Processing from selection of a file until composition of dose distributions (Steps 601–603) is similar to the above-described processing (for example, Steps 201–203 of FIG. 2), and its description is omitted.

[Step 604] Designation of a Tissue

By picking a tissue in a three-dimensional display part, the tissue in question is designated as a tissue for which DVH is to be displayed.

[Step 605] Display of a DVH-Composition Ratio Relation

A relation between DVH and the composition ratio for the designated tissue is displayed stereoscopically.

[Step 606] Judgment of Tissue Designation

When a tissue is to be designated anew, the flow returns to Step 604. Otherwise, the flow proceeds to Step 607.

[Step 607] Judgment of Composition Ratio Setting

When the weight setting button for setting respective weights of irradiation directions is clicked, or when the composition ratio scroll bar is dragged, then, the flow returns to Step 602. Otherwise, the flow proceeds to Step 608.

Thereafter, processing in Steps 608–610 follows. The processing in Steps 608–610 is similar to the above-described processing in Steps 214–215 of FIG. 2, and its description is omitted.

As described above, according to the present invention, in the course of determining contributions by proton beam irradiation and X-ray irradiation, the composition ratio of both dose distributions can be determined based on visual information such as three-dimensional display, an isodose map, a dose profile, and DVH. Thus, the best irradiation conditions can be easily determined.

What is claimed is:

1. A mixed irradiation evaluation support system for supporting judgment and determination of allocation of contribution in mixed irradiation using proton beams and X-rays, comprising:

a complex apparatus for composing dose distributions of proton beams and X-rays in a human body, according to a designated composition ratio; and a display for displaying a composite dose distribution three-dimensionally.

2. A mixed irradiation evaluation support system for supporting judgment and determination of allocation of contribution in mixed irradiation using proton beams and X-rays, comprising:

a complex apparatus for composing dose distributions of proton beams and X-rays in a human body, according to a designated composition ratio; and a display for displaying an isodose map in a designated cross section in the human body with respect to a composite dose distribution.

3. A mixed irradiation evaluation support system for supporting judgment and determination of allocation of contribution in mixed irradiation using proton beams and X-rays, comprising:
a complex apparatus for composing dose distributions of proton beams and X-rays in a human body; and
a display for displaying a dose distribution on a designated line in the human body, with respect to a designated range of a composition ratio.

4. A mixed irradiation evaluation support system for supporting judgment and determination of allocation of contribution in mixed irradiation using proton beams and X-rays, comprising:
a complex apparatus for composing dose distributions of proton beams and X-rays in a human body; and
a display for displaying a dose value at a designated point in the human body, with respect to a designated range of a composition ratio.

5. A mixed irradiation evaluation support system for supporting judgment and determination of allocation of contribution in mixed irradiation using proton beams and X-rays, comprising:
a complex apparatus for composing dose distributions of proton beams and X-rays in a human body; and
a display for displaying DVH for a designated tissue in the human body, with respect to a designated range of a composition ratio.

6. A mixed irradiation evaluation support system, comprising:
a complex apparatus for composing dose distributions of proton beams and X-rays in a human body; and
a display apparatus for displaying a composite dose distribution three-dimensionally.

7. A mixed irradiation evaluation support system, comprising:
a complex apparatus for composing dose distributions of proton beams and X-rays in a human body; and
a display apparatus for displaying an isodose map in a designated cross section in the human body with respect to a composite dose distribution.

8. A mixed irradiation evaluation support system, comprising:
a complex apparatus for composing dose distributions of proton beams and X-rays in a human body; and
a display apparatus for displaying a dose distribution on a designated line in the human body, with respect to a designated range.

9. A mixed irradiation evaluation support system, comprising:
a complex apparatus for composing dose values of proton beams and X-rays in a human body; and
a display apparatus for displaying a dose value at a designated point in the human body, with respect to a designated range.

10. A mixed irradiation evaluation support system, comprising:
a complex apparatus for composing dose distributions of proton beams and X-rays in a human body; and
a display apparatus for displaying DVH for a designated tissue in the human body, with respect to a designated range.

11. A mixed irradiation evaluation support system, comprising:
a complex apparatus for composing dose distributions of proton beams and X-rays in a human body, according to a designated composition ratio; and
a display apparatus for displaying a composite dose distribution three-dimensionally.

12. A mixed irradiation evaluation support system, comprising:
a complex apparatus for composing dose distributions of proton beams and X-rays in a human body, according to a designated composition ratio; and
a display apparatus for displaying an isodose map in a designated cross section in the human body with respect to a composite dose distribution.

13. A mixed irradiation evaluation support system, comprising:
a complex apparatus for composing dose distributions of proton beams and X-rays in a human body; and
a display apparatus for displaying a dose distribution on a designated line in the human body, with respect to a designated range of a composition ratio.

14. A mixed irradiation evaluation support system, comprising:
a complex apparatus for composing dose value of proton beams and X-rays in a human body; and
a display apparatus for displaying a dose value at a designated point in the human body, with respect to a designated range of a composition ratio.

15. A mixed irradiation evaluation support system, comprising:
a complex apparatus for composing dose distributions of proton beams and X-rays in a human body; and
a display apparatus for displaying DVH for a designated tissue in the human body, with respect to a designated range of a composition ratio.

16. A mixed irradiation evaluation support system, comprising:
a complex apparatus for composing dose distributions of proton beams and X-rays in a human body; and
a display apparatus for displaying a composite dose distribution.

17. A mixed irradiation evaluation support system according to claim 16, wherein
said display apparatus displays dose distributions of proton beams and X-rays in a human body.

18. A mixed irradiation evaluation support system according to claim 16, wherein
said display apparatus displays said composite dose distribution and said dose distributions of proton beams and X-rays in a human body, using different colors.

19. A mixed irradiation evaluation support system according to claim 16, wherein
said display apparatus displays tissue designated.

20. A mixed irradiation evaluation support system according to claim 16, wherein
said dose distribution is a dose distribution having dose values larger than a designated value.

* * * * *